United States Patent [19]

Lysenko

[11] Patent Number: 4,835,306

[45] Date of Patent: May 30, 1989

[54] PREPARATION OF 3-AMINO-4-HYDROXYBENZOIC ACIDS

[75] Inventor: Zenon Lysenko, Midland, Mich.

[73] Assignee: The Dow Chemical Company, Midland, Mich.

[21] Appl. No.: 827,996

[22] Filed: Feb. 10, 1986

[51] Int. Cl.$^4$ .............................................. C07C 99/00
[52] U.S. Cl. .................................... 562/453; 562/434; 562/438
[58] Field of Search ....................... 562/438, 434, 453; 560/24, 23

[56] References Cited

U.S. PATENT DOCUMENTS

| | | | |
|---|---|---|---|
| 2,652,332 | 9/1954 | Olcott et al. | 560/23 |
| 3,345,157 | 10/1967 | Richter | 562/453 |
| 3,391,186 | 7/1968 | Thominet | 562/453 |
| 3,822,311 | 7/1974 | Wedemeyer et al. | 562/438 |
| 3,882,171 | 5/1975 | Levy | 562/453 |
| 3,928,395 | 12/1975 | Seha et al. | 562/453 |
| 3,929,864 | 12/1975 | Popenfuss | 562/453 |
| 4,036,838 | 7/1977 | Vogel et al. | 560/23 |

OTHER PUBLICATIONS

Morrison et al., "Organic Chemistry", Allyn & Bacon, Inc., p. 797 (1966).
Oie et al, Chem. Abst; vol. 75, #76302 (1971).

*Primary Examiner*—James H. Reamer

[57] ABSTRACT

This invention is a process for the preparation of a 3-amino-4-hydroxybenzoic acid which comprises
 (a) contacting a p-halobenzoic acid with nitric acid in an acidic reaction medium under conditions such that a 3-nitro-4-halobenzoic acid is prepared;
 (b) contacting the 3-nitro-4-halobenzoic acid with an alkali metal hydroxide in a reaction medium under conditions such that the halo moiety is replaced with a hydroxide moiety, to prepare a 3-nitro-4-hydroxybenzoic acid, or salt thereof; and
 (c) reducing the 3-nitro-4-hydroxybenzoic acid under conditions such that a 4-hydroxy-3-aminobenzoic acid is prepared.

16 Claims, No Drawings

PREPARATION OF 3-AMINO-4-HYDROXYBENZOIC ACIDS

BACKGROUND OF THE INVENTION

This invention relates to a process for the preparation of 3-amino-4-hydroxybenzoic acids.

Papenfuss, U.S. Pat. No. 3,929,864 discloses a process for the preparation of 4-hydroxy-3-nitrobenzoic acid alkyl esters wherein 4-hydroxybenzoic alkyl esters are contacted with nitric acid at about 0° C. to 60° C. wherein the nitric acid has a strength of 30 to 62 percent by weight so as to prepare 4-hydroxy-3-nitrobenzoic acid alkyl esters. These compounds can be used directly for further reactions, for example, subjected to catalytic hydrogenation to give 4-hydroxy-3-aminobenzoic acid esters.

The Papenfuss process suffers from the drawback of over-nitration and of decarboxylation of the starting material. Purification of the product of the Papenfuss process is difficult and tedious.

3-Amino-4-hydroxybenzoic acids are useful in the preparation of AB polybenzoxazole ordered polymers. Previous methods used to prepare such compounds afford such compounds in low yields requiring extensive purification so that they may be rendered suitable for polymerization. It has been discovered that the presence of impurities in 3-amino-4-hydroxybenzoic acids prevent the formation of high molecular weight AB polybenzoxazoles. What is needed is a process which prepares 3-amino-4-hydroxybenzoic acids in high yields with high purity.

SUMMARY OF THE INVENTION

This invention is a process for the preparation of a 3-amino-4-hydroxybenzoic acid which comprises (a) contacting a p-halobenzoic acid or ester thereof, which is unsubstituted or substituted with one or two alkyl groups, with the proviso that at least one of the positions ortho to the halo moiety is unsubstituted, with nitric acid in an acidic reaction medium, as herein defined, under conditions such that a 3-nitro-4-halobenzoic acid or ester thereof is prepared;

(b) contacting the 3-nitro-4-halobenzoic acid or ester thereof with an alkali metal hydroxide in a reaction medium under conditions such that the halo moiety is replaced with a hydroxide moiety or a salt thereof, to prepare a 3-nitro-4-hydroxybenzoic acid, or salt thereof; and (c) reducing the 3-nitro-4-hydroxybenzoic acid or salt thereof in a reaction medium under conditions such that a 4-hydroxy-3-aminobenzoic acid is prepared.

The process of this invention results in the surprising preparation of 3-amino-4-hydroxybenzoic acids in high yield and very high purity. Such highly pure products are useful in the preparation of high molecular weights AB polybenzoxazoles without extensive and difficult purification.

DETAILED DESCRIPTION OF THE INVENTION

In the first step of the process, a p-halobenzoic acid or ester thereof which is unsubstituted or substituted with one or two alkyl groups is contacted with nitric acid in an acidic reaction medium to prepare a 3-nitro-4-halobenzoic acid or ester thereof. Suitable starting materials include any p-halobenzoic acid or ester thereof, wherein the benzene ring is unsubstituted or substituted with one or two alkyl groups, provided that at least one of the positions ortho to the halo moiety is unsubstituted. "Halo" refers herein to chlorine, bromine, iodine and fluorine. Preferred p-halobenzoic acids or esters thereof correspond to the formula

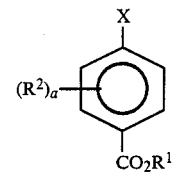

wherein
$R^1$ is separately in each occurrence hydrogen or alkyl;
$R^2$ is separately in each occurrence alkyl;
X is separately in each occurrence a halogen; and
a is the integer 0, 1 or 2,
with the proviso that at least one of the positions ortho to the halo moiety is unsubstituted.

Examples of p-halobenzoic acids or esters thereof useful in this invention include p-chloro-2-methylbenzoic acid, p-chloro-2-ethylbenzoic acid, p-chloro-2-propylbenzoic acid, p-bromo-2-methylbenzoic acid, p-bromo-2-ethylbenzoic acid, p-bromo-2-propylbenzoic acid, methyl p-chloro-2-methylbenzoate, methyl p-chloro-2-ethylbenzoate, methyl p-chloro-2-propylbenzoate, ethyl p-chloro-2-methylbenzoate, ethyl p-chloro-2-ethylbenzoate, ethyl p-chloro-2-propylbenzoate, propyl p-chloro-2-methylbenzoate, propyl p-chloro-2-ethylbenzoate, propyl p-chloro-2-propylbenzoate, methyl p-bromo-3-methylbenzoate, methyl p-bromo-3-ethylbenzoate, methyl p-bromo-3-propylbenzoate, ethyl p-bromo-3-methylbenzoate, ethyl p-bromo-3-ethylbenzoate, ethyl p-bromo-3-propylbenzoate, propyl p-bromo-3-methylbenzoate, propyl p-bromo-3-ethylbenzoate, and propyl p-bromo-3-propylbenzoate. Preferred are the p-halobenzoic acids which do not have alkyl substituents with p-chlorobenzoic acid being most preferred.

The products prepared by this step are the 3-nitro-4-halobenzoic acids or esters thereof which may be unsubstituted or further substituted with one or two alkyl groups. Preferred 3-nitro-4-halobenzoic acids or esters thereof correspond to the formula

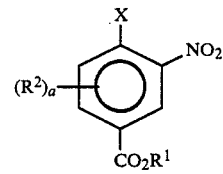

wherein $R^1$, $R^2$, a and X are as hereinbefore defined. Examples of preferred 3-nitro-4-halobenzoic acids or esters thereof include 3-nitro-4-halobenzoic acid, 3-nitro-4-chloro-2-methylbenzoic acid, 3-nitro-4-chloro-2-ethylbenzoic acid, 3-nitro-4-chloro-2-propylbenzoic acid, 3-nitro-4-bromo-3-methylbenzoic acid, 3-nitro-4-bromo-3-ethylbenzoic acid, 3-nitro-4-bromo-3-propylbenzoic acid, methyl p-chloro-2-methylbenzoate, methyl 3-nitro-4-chloro-2-ethylbenzoate, methyl 3-nitro-4-chloro-2-propylbenzoate, ethyl 3-nitro-4- chloro-2-methylbenzoate, ethyl p-chloro-2-ethylbenzoate, ethyl 3-nitro-4-chloro-2-propylbenzoate, propyl 3-nitro-4-chloro-2-methylbenzoate, propyl p-chloro-2-ethylbenzoate, propyl 3-nitro-4-chloro-2-propylbenzoate, methyl 3-nitro-4-bromo-3-methylbenzoate, methyl 3-nitro-4-bromo-5-ethylbenzoate, methyl 3-nitro-4-bromo-5-propylbenzoate, ethyl 3-nitro-4-bromo-5-methylbenzoate, ethyl 3-nitro-4-bromo-5-ethylbenzoate, ethyl 3-nitro-4-bromo-5-propylbenzoate, propyl 3-nitro-4-bromo-5-methylbenzoate, propyl 3-nitro-4-bromo-5-ethylbenzoate, propyl 3-nitro-4-bromo-5-propylbenzoate, 3-nitro-4-chloro-6-methylbenzoic acid, 3-nitro-4-chloro-6-ethylbenzoic acid, 3-nitro-4-chloro-6-propylbenzoic acid, 3-nitro-4-bromo-6-methylbenzoic acid, 3-nitro-4-bromo-6-ethylbenzoic acid, 3-nitro-4-bromo-6-propylbenzoic acid, methyl 3-nitro-4-chloro-6-methylbenzoate, methyl 3-nitro-4-chloro-6-ethylbenzoate, methyl 3-nitro-4-chloro-6-propylbenzoate, ethyl 3-nitro-4-chloro-6-methylbenzoate, ethyl 3-nitro-4-chloro-6-ethylbenzoate, ethyl 3-nitro-4-chloro-6-propylbenzoate, propyl 3-nitro-4-chloro-6-methylbenzoate, propyl 3-nitro-4-chloro-6-ethylbenzoate, and propyl 3-nitro-4-chloro-6-propylbenzoate. Preferred are the 3-nitro-4-halobenzoic acids with 3-nitro-4-chlorobenzoic acid being most preferred.

The process of step 1 can be exemplified by the following equation

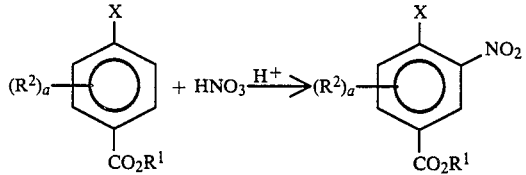

wherein $R^1$, $R^2$, X and a are as hereinbefore defined. The p-halobenzoic acid or ester thereof is reacted with a sufficient amount of nitric acid so as to prepare the desired 3-nitro-4-halobenzoic acid or ester thereof. Preferably, at least one equivalent of nitric acid per equivalent of p-halobenzoic acid or ester thereof is used. A slight excess of nitric acid is desirable so as to drive the reaction to completion with respect to the p-halobenzoic acid or ester thereof. This process is performed in the presence of an acidic reaction medium.

An acidic reaction medium is a liquid medium which allows at least some nitration to occur upon the agitated contact of (1) 1 liter of acidic reaction medium, (2) 500 g of powdered (1-2 micron) p-chlorobenzoic acid and 1 drop of 1.0 Normal nitric acid at atmospheric pressure and a temperature of 30° C. Preferably, the acidic reaction medium contains more than about 20 weight percent of a Lewis or Bronsted acid, based on the weight of the acidic reaction medium; more preferably more than about 50 weight percent, even more preferably more than about 70 weight percent and most preferably more than about 90 weight percent. Preferably, the Lewis or Bronsted acid is a Bronsted acid, more preferably $H_2SO_4$, HCl, HOAc, $H_3PO_4$, $CH_3SO_3H$, fuming nitric acid, HBr, HF, HI and the like and most preferably $H_2SO_4$. Preferably, the $H_2SO_4$ is in excess. Excess sulfuric acid means greater than about 1 equivalent of sulfuric acid per equivalent of p-halobenzoic acid, preferably the ratio of sulfuric acid to p-halobenzoic acid or ester thereof is 1.3:1 or greater. Any remainder of the acid reaction medium, that is any nonacid portion of the acid reaction medium, is anything which allows the formation of an acid reaction medium. Preferably, the remainder is an organic liquid or water with water being most preferred.

In some instances the p-halobenzoic acid or ester thereof is insoluble in a given acidic reaction medium. If this is the case, it is preferred that the p-halobenzoic acid or ester thereof be ground into a powder (1-2 microns) and suspended in the reaction medium.

This process can be run at any temperature at which the desired product is prepared. Preferable temperatures are between about $-10°$ C. and 50° C., with between about $-6°$ C. and 40° C. being more preferred, with between about 15° C. and 40° C. being most preferred.

The reactants are contacted for a time sufficient to allow the desired formation of 3-nitro-4-halobenzoic acid or ester thereof. Preferable reaction times are between about 2 and 48 hours, with between about 9 and 36 hours being most preferred.

The 3-nitro-4-halobenzoic acid or ester thereof can be recovered by diluting the reaction medium with a small amount of water, preferably between about 25 and about 100 percent by volume, and more preferably about 25 percent by volume, so as to result in complete precipitation of the desired product. The product can thereafter be recovered by filtration, and thereafter washed with water. The product may optionally be dried by any means well-known in the art, although drying is not necessary.

The 3-nitro-4-halobenzoic acid, or ester thereof, so prepared is thereafter contacted with an alkali metal hydroxide in a reaction medium so as to replace the halo moiety with a hydroxide moiety or a salt thereof, therefore preparing a 3-nitro-4-hydroxybenzoic acid, or salt thereof. Such 3-nitro-4-hydroxybenzoic acid or salt thereof, can further be substituted by one or two alkyl groups. Preferred 3-nitro-4-hydroxybenzoic acids, or salts thereof, correspond to the formula

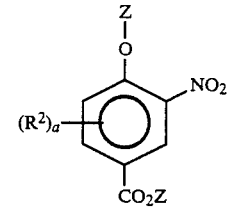

wherein $R^1$, $R^2$ and a are as hereinbefore defined, and Z is separately in each occurrence hydrogen or a cation. Examples of preferred 3-nitro-4-hydroxybenzoic acids, or salts thereof include 3-nitro-4-hydroxybenzoic acid, 2-methyl-3-nitro-4-hydroxybenzoic acid, 5-methyl-3-nitro-4-hydroxybenzoic acid, 6-methyl-3-nitro-4-hydroxybenzoic acid, 2-ethyl-3-nitro-4-hydroxybenzoic acid, 5-ethyl-3-nitro-4-hydroxybenzoic acid, 6-ethyl-3-nitro-4-hydroxybenzoic acid, 2-propyl-3-nitro-4-hydroxybenzoic acid, 5-propyl-3-nitro-4-hydroxybenzoic acid and 6-propyl-3-nitro-4-hydroxybenzoic acid, or alkali earth metal salts thereof. The preferred acid is the 3-nitro-4-hydroxybenzoic acid.

The process of this step is generally represented by the equation

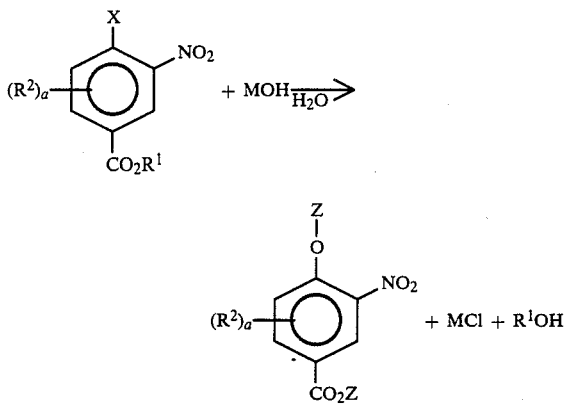

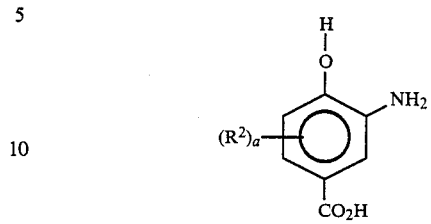

wherein M is an alkali metal, and $R^1$, $R^2$, X, Z and a are as hereinbefore defined. The 3-nitro-4-halobenzoic acid or ester thereof is reacted with at least a 3 equivalent excess of an alkali metal hydroxide. In that embodiment wherein $R^1$ is hydrogen, wherein the starting material is a benzoic acid, 3 equivalents or more of alkali metal hydroxide is suitable. In that embodiment where $R^1$ is an alkyl group, that is, wherein the starting material is a benzoate ester, at least 4 equivalents of alkali metal hydroxide is preferred. The process can be run with any amount of alkali metal hydroxide which gives the desired product, but it has been discovered that at least a 1 to 4, equivalent excess results in driving the reaction to completion with respect to the benzoic acid, or benzoate ester, respectively. Wherein the starting material is a benzoic acid, it is preferred to use between about 4.5 and 5.5 equivalents of alkali metal hydroxide for each equivalent of benzoic acid. Wherein the starting material is a benzoate ester, it is preferred to use between about 5.5 and 6.5 equivalents of alkali metal hydroxide for each equivalent of benzoate ester. Preferred alkali metal hydroxides are sodium hydroxide, potassium hydroxide, lithium hydroxide, cesium hydroxide and rubidium hydroxide with sodium hydroxide being most preferred.

This process takes place in a reaction medium. A sufficient amount of reaction medium which allows the reactants to react may be used. Preferable reaction media include inert solvents and water, with water being more preferred.

This process is performed at any temperature at which the desired product is formed. Preferred temperatures are between about 65° C. and 120° C., more preferably higher than 90° C. and/or less than 110° C., and about 103° C. being most preferred. In the most preferred embodiment, the reaction is run at reflux in water. The product may be recovered by contacting the reaction medium with a sufficient amount of strong protic mineral acid to result in a 3–12N solution, preferably a 6–12N solution of the acid. Suitable acids include hydrochloric acid, hydrobromic acid, sulfuric acid, nitric acid, and the like. The preferred acid is hydrochloric acid. The product is recovered in the acidic form as it precipitates from solution.

In the third step of the process of this invention, the 3-nitro-4-hydroxybenzoic acid, or salt thereof, is reduced to the 3-amino-4-hydroxybenzoic acid. The product is a 3-amino-4-hydroxybenzoic acid, which can be substituted with one or two alkyl groups. 3-Amino-4-hydroxybenzoic acid as referred to herein further refers to the amine salts of the 3-amino-4-hydroxybenzoic acid, as such compound is generally recovered in the amine salt form. Preferred 3-amino-4-hydroxybenzoic acids correspond to the formula wherein $R^2$ and a are as hereinbefore defined. Examples of preferred 3-amino-4-hydroxybenzoic acids prepared by this process include 3-amino-4-hydroxybenzoic acid, 2-methyl-3-amino-4-hydroxybenzoic acid, 5-methyl-3-amino-4-hydroxybenzoic acid, 6-methyl-3-amino-4-hydroxybenzoic acid, 2-ethyl-3-amino-4-hydroxybenzoic acid, 5-ethyl-3-amino-4-hydroxybenzoic acid, 6-ethyl-3-amino-4-hydroxybenzoic acid, 2-propyl-3-amino-4-hydroxybenzoic acid, 5-propyl-3-amino-4-hydroxybenzoic acid and 6-propyl-3-amino-4-hydroxybenzoic acid. The preferred species is a 3-amino-4-hydroxybenzoic acid. The nitro groups on the 3-nitro-4-hydroxybenzoic acids, or salts thereof, may be reduced to an amine by any means known in the art. One particularly useful means is by contacting hydrogen or a source of hydrogen gas with the 3-nitro-4-hydroxybenzoic acid or salt thereof in an aqueous solution in the presence of a hydrogenation catalyst. A preferred class of hydrogenation catalysts are one or more of the Group VIII metal(s) such as palladium and platinum with palladium and platinum being most preferred. It is preferred that the metal(s) be supported. Preferable supports include aluminas, zeolites, silicas, silica gels, silicalite, activated carbons, and diatomaceous earth. More preferred supports are zeolites, silicas, aluminas or activated carbons, with activated carbon being most preferred. The preferred hydrogenation catalyst is palladium-on-carbon. The catalysts may be loaded in any concentration whch gives the desired reduction. Preferred catalysts loadings are between about 0.01 and 10 percent by weight, more preferably between about 1.0 and 5.0 with 5.0 percent being most preferred. The reaction pressure is that suitable for reducing the nitro moiety to an amine moiety. Preferred reaction pressures are between about atmospheric and 200 psi with between about atmospheric and 50 psi being most preferred. Reaction temperatures are those at which the reaction proceeds, preferred reaction temperatures are between about 20° C. and 150° C., with between about 90° C. and 110° C. being the most preferred.

Another method of reduction involves contacting the 3-nitro-4-hydroxybenzoic acid salt with aluminum in the zero-valent state, preferably aluminum metal in basic aqueous solution. The amount of aluminum metal is that amount sufficient to result in complete reduction of the nitro moiety to an amine moiety. Preferably, aluminum is present in a ratio of aluminum to the 3-nitro-4-hydroxybenzoic acid salt of 2:1 or greater; most preferably the aluminum metal is present in a ratio of aluminum metal to 3-nitro-4-hydroxybenzoic acid salt of between about 2.2:1 and 3:1. This contacting can be performed at any temperature at which the reduction occurs. Preferred temperatures are between about 15° C. and 100° C., with most preferred temperatures being between about 25° C. and 75° C. This process may take place at any pressure, preferred pressure is atmospheric. The 3-amino-4-hydroxybenzoic acid may be recovered as a salt of the amine by contacting the reaction solution with a strong protic mineral acid, or a source thereof. Generally, a sufficient amount of strong protic mineral acid is added to render the normality of the solution between about 3 and 12, preferably between about 3 and 6. In this embodiment, the desired amine salt precipitates from solution and can be recovered by filtration. The product may thereafter be purified by recrystallization.

In that embodiment where aluminum in a zero-valent state is used to reduce the nitro moiety, the 3-nitro-4-hydroxybenzoic acid, or salt thereof, need not be recovered from the reaction solution of step 2. In fact, such reaction solution can immediately be contacted with the aluminum reduction catalyst so as to result in the reduction of the nitro group to the amine. After such reduction has been completed, then the product can be recovered as described hereinbefore.

Suitable strong protic mineral acids include hydrochloric acid, hydrobromic acid, hydroiotic acid, nitric acid, sulfuric acid, and the like. The most preferred acid is hydrochloric acid. The strong protic mineral acid may be added in concentrated form or may be added to the solution or may be added in the nonacidic form, for example, hydrogen chloride may be bubbled through the reaction solution so as to render the reaction solution between 3N and 12N.

$R^1$ is preferably hydrogen, $C_{1-10}$ alkyl, more preferably hydrogen, $C_{1-3}$ alkyl, and most preferably hydrogen. $R_2$ is preferably $C_{1-10}$ alkyl, and most preferably $C_{1-3}$ alkyl. Preferably a is 0 or 1, and most preferably 0. X is preferably chlorine, bromine, or iodine, more preferably chlorine or bromine, and most preferably chlorine. Z is preferably H or an alkali metal cation, and more preferably H, a sodium cation or potassium cation.

One significant advantage of this process is that there is no need to purify the products of the intermediate steps. Furthermore, the product of the final step can easily be purified by one simple recrystallization.

Typical yields are in excess of about 90 mole percent based on starting p-halobenzoic acid or ester thereof. Preferred yields are in excess of about 95 mole percent. Typical purity of 3-amino-4-hydroxybenzoic acid is in excess of 95 weight percent, more preferably 99 weight percent and most preferably 99.95 weight percent.

Specific Embodiments

The following examples are included for illustrative purposes only and are not intended to limit the scope of the invention. Unless otherwise indicated, all parts and percentages are by weight.

EXAMPLE 1

Preparation of 3-amino-4-hydroxybenzoic acid hydrochloride from 4-chlorobenzoic acid A—Preparation of 4-chloro-3-nitrobenzoic acid To a 2-liter, 3-necked, round-bottom flask is added 680 ml of concentrated $H_2SO_4$ and 400 g of p-chlorobenzoic acid. The mixture is stirred and brought to 0° C. by means of a constant temperature bath. A solution of concentrated $HNO_3$ (216 ml) and concentrated $H_2SO_4$ (216 ml) is added dropwise to the reaction mixture at such a rate as to maintain the temperature between 10° C. and 25° C. Upon completion of the addition, the reaction temperature is raised to 37° C. and the mixture is allowed to stir for a period of 10–14 hours. The reaction mixture is then poured over crushed ice and the product, 4-chloro-3-nitrobenzoic acid, is filtered and dried, having a yield of 525.7 g or 98.7 percent with a melting point of 178° C.–180° C. This material is used without further purification.

B—Preparation of 4-hydroxy-3-nitrobenzoic acid

To a 5-liter, 3-necked, round-bottom flask is added 532 g of NaOH in 3 liters of water and 520 g of 4-chloro-3-nitrobenzoic acid. The solution is heated to reflux (100° C.) under nitrogen and stirred for 10 hours. Upon completion, the reaction is cooled to room temperature and neutralized with concentrated hydrochloric acid. The product is isolated by filtration, washed with 3 liters of cold water and dried in a vacuum oven at 30° C. overnight at 3 mm Hg. The yield is 430 g (90 percent) of 4-hydroxy-3-nitrobenzoic acid with a melting point of 182° C.–183° C.

C—Preparation of 3-amino-4-hydroxybenzoic acid hydrochloride

To a 5-liter, 3-necked, round-bottom flask is added 160 g of 4-hydroxy-3-nitrobenzoic acid, 150 cc concentrated hydrochloric acid, 3 liters of distilled water and 25 g of 5 percent palladium on carbon. The reaction mixture is heated to 95° C. with vigorous stirring and hydrogen gas is passed into the reaction mixture. Upon completion, the reaction is cooled to room temperature under nitrogen gas and the catalyst is recovered by filtration. The resulting solution is poured into two 4-liter beakers and acidified with concentrated hydrochloric acid to a normality of 4 and allowed to cool to 0° C. The resulting solid is isolated by filtration and dried under vacuum to afford 176 g of crude 3-amino-4-hydroxybenzoic acid hydrochloride monohydrate with a melting point of 300° C. decomposition.

D—Recrystallization of 3-amino-4-hydroxybenzoic acid hydrochloride

The product obtained in the previous reaction is placed in a 2-liter, round-bottom flask containing 800 ml of water, 17.6 g of $SnCl_2 \cdot 2H_2O$, 535 cc of concentrated hydrochloric acid and 20 g of decolorizing carbon. The mixture is heated to reflux and kept for a period of 15 minutes, after which time the carbon is removed by filtration and the solution is cooled slowly to 0° C. The 3-amino-4-hydroxybenzoic acid hydrochloride is isolated by filtration as the monohydrate in 90 mole percent recovered yield (162 g) with a melting point of 300° C. decomposition.

EXAMPLE 2

Preparation of 3-amino-4-hydroxybenzoic acid hydrochloride from 4-chloromethylbenzoate A—Preparation of 4-chloro-3-nitromethylbenzoate To a one-liter, 3-necked, round-bottom flask is charged 130 g of p-chloromethylbenzoate in 220 ml of $H_2SO_4$. The solution is cooled to −5° C. by means of a constant temperature bath and kept under nitrogen. A solution consisting of 70 ml of concentrated $HNO_3$ and 70 ml of concentrated $H_2SO_4$ is added dropwise at such a rate as to maintain the temperature of the reaction below 15° C. When the addition is completed, the reaction mixture is poured over crushed ice (500 g). The resulting precipitate is isolated by filtration and washed with 300 ml of cold water and dried to afford 160 g of 4-chloro-3-nitromethylbenzoate in 99 mole percent yield having a melting point of 78° C.–80° C. This material is used without further purification.

B—Preparation of 4-hydroxy-3-nitrobenzoic acid

A 5-liter, 3-necked, round-bottom flask is charged with 432 g of NaOH, 3 liters of H$_2$O and 320 g of 4-chloro-3-nitromethylbenzoate. The reaction mixture is heated to 95° C. for a period of 4 hours under a nitrogen atmosphere. After this time, the reaction is poured over 500 g of crushed ice and 750 ml of concentrated hydrochloric acid. The precipitate which forms is isolated by filtration, washed with 500 ml of cold water and dried at 30° C. under vacuum at 3 mm Hg. The resulting 4-hydroxy-3-nitrobenzoic acid is isolated in 91 mole percent yield (245 g) having a melting point of 182° C.–183° C.

C—Preparation of 3-amino-4-hydroxybenzoic acid hydrochloride

To a 5-liter, 3-necked, round-bottom flask is added 160 g of 4-hydroxy-3-nitrobenzoic acid, 150 cc hydrogen chloride, 3 liter of distilled water and 25 g of 5 percent palladium on carbon. The reaction mixture is heated to 95° C. with vigorous stirring and hydrogen gas is passed into the reaction mixture. Upon completion, the reaction is cooled to room temperature under nitrogen gas and the catalyst is recovered by filtration. The resulting solution is poured into two 4-liter beakers and acidified with concentrated hydrochloric acid to a normality of 4 and allowed to cool to 0° C. The resulting solid is isolated by filtration and dried under vacuum to afford 176 g of crude 3-amino-4-hydroxybenzoic acid hydrochloride monohydrate with a melting point of 300° C. decomposition.

D—Recrystallization of 3-amino-4-hydroxybenzoic acid hydrochloride

The product obtained in the previous reaction is placed in a 2-liter, round-bottom flask containing 800 ml of water, 17.6 g of SnCl$_2$ 2H$_2$O, 535 cc of concentrated hydrochloric acid and 20 g of decolorizing carbon. The mixture is heated to reflux and kept for a period of 15 minutes, after which time the carbon is removed by filtration and the solution is cooled slowly to 0° C. The 3-amino-4-hydroxybenzoic acid hydrochloride is isolated by filtration as the monohydrate in 95 mole percent recovered yield (162 g) with a melting point of 300° C. decomposition.

EXAMPLE 3

A—Preparation of 3-amino-4-hydroxybenzoic acid hydrochloride by aluminum reduction 4-Chloro-3-nitrobenzoic acid is prepared as described in Examples 1A and 1B above.

B—Preparation of 3-amino-4-hydroxybenzoic acid hydrochloride

A 5-liter, 3-necked flask is charged with 227 g of 3-chloro-4-nitrobenzoic acid, 3 liters of water and 250 g of solid KOH, and heated to reflux under a nitrogen atmosphere. The reaction is maintained at this temperature for a period of 9½ hours after which time the reaction is cooled to 70° C. Aluminum metal (67 g) is slowly added to the reaction at such a rate as to maintain the temperature at 95° C. Upon completion of this addition, the reaction mixture is filtered and the aqueous portion is acidified with concentrated hydrogen chloride and allowed to cool to 0° C. The crude 3-amino-4-hydroxybenzoic acid hydrochloride is isolated by filtration and dried. The yield of product is 222 g or 91 mole percent as the monohydrate.

C—Recrystallization of 3-amino-4-hydroxybenzoic acid hydrochloride

Recrystallization of 3-amino-4-hydroxybenzoic acid hydrochloride is accomplished as described in Examples 1 and 2 with a recovery of 202 g or 91 mole percent, based on the amount charged, having a melting point of 300° C. with decomposition.

EXAMPLE 4

To a 5-liter, 3-necked, round-bottom flask, equipped with a stirrer and thermometer, is added 2.0 liters of concentrated H$_2$SO$_4$ and 800 g of powdered (about 1–2 microns) p-chlorobenzoic acid. The mixture is stirred and cooled to 0° C. in an oil bath. To the cooled mixture is added 432 ml of 71 weight percent nitric acid in water solution dropwise. The nitric acid solution is added at a rate slow enough to maintain the temperature lower than about 30° C. Upon completion of adding nitric acid, the temperature is raised to 37° C. over 3 hours. The reaction mixture is then cooled to 15° C. To the cooled mixture is added 0.75 liter of room temperature water at a rate so as to keep the reaction temperature below about 40° C. The product is isolated by filtration using fritted glass funnel and washed with 1.5 liters of room temperature water. The washed product is air-dried until a constant weight is observed to yield 1.0174 kg of 4-chloro-3-nitrobenzoic acid, which has a melting point of 178° C.–179.5° C. This is a yield of 99 mole percent. This material can be used without further purification.

What is claimed is:

1. A process for the preparation of a 3-amino-4-hydroxybenzoic acid which comprises
   (a) contacting a p-halobenzoic acid or ester thereof, which is unsubstituted or substituted with one or two alkyl groups, with the proviso that at least one of the positions ortho to the halo moiety is unsubstituted, with nitric acid in an acidic reaction medium under conditions such that a 3-nitro-4-halobenzoic acid or ester thereof is prepared;
   (b) contacting the 3-nitro-4-halobenzoic acid or ester thereof with an alkali metal hydroxide in a reaction medium under conditions such that the halo moiety is replaced with a hydroxide moiety or a salt thereof, to prepare a 3-nitro-4-hydroxybenzoic acid, or salt thereof; and
   (c) reducing the 3-nitro-4-hydroxybenzoic acid or salt thereof under conditions such that a 4-hydroxy-3-aminobenzoic acid is recovered in purity in excess of 95 weight percent.

2. The process of claim 1 in which the 3-amino-4-hydroxybenzoic acid is recovered in a purity in excess of 99 weight percent.

3. The process of claim 2 wherein the p-halobenzoic acid or ester thereof corresponds to the formula

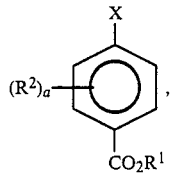

the 3-nitro-4-halobenzoic acid or ester thereof corresponds to the formula

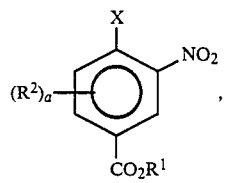

the 3-nitro-4-hydroxybenzoic acid or salt thereof corresponds to the formula

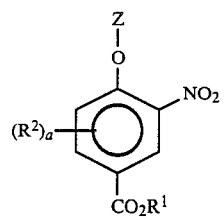

and the 3-amino-4-hydroxybenzoic acid corresponds to the formula

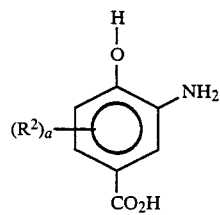

wherein $R^1$ is separately in each occurrence hydrogen or alkyl;

$R^2$ is separately in each occurrence alkyl;

X is separately in each occurrence a halogen;

Z is separately in each occurrence hydrogen or a cation; and a is the integer 0, 1 or 2.

4. The process of claim 3 wherein each equivalent of p-halobenzoic acid or ester thereof is contacted with at least about 1 equivalent of nitric acid and in excess of 1 equivalent of sulfuric acid.

5. The process of claim 4 wherein each equivalent of 3-nitro-4-halobenzoic acid or ester thereof is reacted with at least about 3 equivalents of alkali metal hydroxide.

6. The process of claim 5 wherein the temperature in step (a) is between about $-10°$ C. and $50°$ C.; and the temperature in step (b) is between about $65°$ C. and $100°$ C.

7. The process of claim 6 wherein the 3-nitro-4-hydroxybenzoic acid is reduced by contacting with hydrogen gas or a source of hydrogen in the presence of a heterogeneous reduction catalyst.

8. The process of claim 7 wherein the heterogeneous reduction catalyst is palladium-on-charcoal.

9. The process of claim 7 wherein the alkali metal salt of 3-nitro-4-hydroxybenzoic acid is recovered from the reaction medium of step (b) by contacting the reaction medium with a strong protic acid so that the 3-nitro-4-hydroxybenzoic acid precipitates from the reaction medium.

10. The process of claim 9 wherein the strong protic acid is hydrochloric acid.

11. The process of claim 6 wherein the 3-nitro-4-hydroxybenzoic acid is reduced by contacting with aluminum in the zero-valent state.

12. The process of claim 11 wherein the aluminum in the zero-valent state is contacted with the 3-nitro-4-hydroxybenzoic acid in the reaction medium of step (b).

13. The process of claim 12 wherein the 3-amino-4-hydroxybenzoic acid is recovered as an amine salt, after reduction by contacting the reaction medium with a sufficient amount of a strong protic mineral acid, to convert the 3-amino-4-hydroxybenzoic acid to an amine salt, and precipitate said salt.

14. The process of claim 6 wherein $R^1$ is hydrogen or $C_{1-10}$ alkyl;

$R^2$ is $C_{1-10}$ alkyl;

X is chlorine, bromine or iodine;

Z is an alkali metal cation; and a is the integer 0 or 1.

15. The process of claim 14 wherein $R^1$ is hydrogen; Z is sodium; and a is 0.

16. The process of claim 1 wherein the p-halobenzoic acid is p-chlorobenzoic acid and the 3-amino-4 hydroxybenzoic acid is represented by the formula:

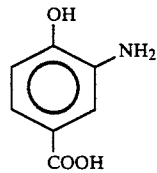

* * * * *

UNITED STATES PATENT AND TRADEMARK OFFICE
CERTIFICATE OF CORRECTION

PATENT NO. : 4,835,306

DATED : May 30, 1989

INVENTOR(S) : Zenon Lysenko

It is certified that error appears in the above-identified patent and that said Letters Patent is hereby corrected as shown below:

Column 1, line 5 please insert --This application is a continuation-in-part of Appln Ser. No 749,079, filed June 26, 1985, now abandoned. --
Column 6, line 42, delete " whch " and insert -- which --
Column 11, lines 24 - 35 delete the formula
"
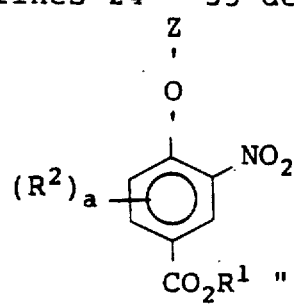
"

and insert therefor
--
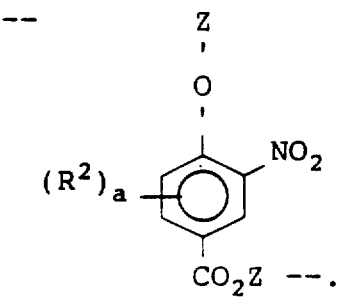
--.

UNITED STATES PATENT AND TRADEMARK OFFICE
CERTIFICATE OF CORRECTION

PATENT NO. : 4,835,306

DATED : May 30, 1989

INVENTOR(S) :

It is certified that error appears in the above-identified patent and that said Letters Patent is hereby corrected as shown below:

Column 12, Claim 16, line 46, delete "-4 hydrox-" and insert -- -4-hydroxy- --.

Signed and Sealed this

Third Day of July, 1990

Attest:

HARRY F. MANBECK, JR.

Attesting Officer

Commissioner of Patents and Trademarks